(12) United States Patent
More

(10) Patent No.: US 7,851,200 B2
(45) Date of Patent: Dec. 14, 2010

(54) BIOREACTOR FOR GROWING ENGINEERED TISSUE

(76) Inventor: Robert B. More, 1811 Running Brook Dr., Austin, TX (US) 78723

( * ) Notice: Subject to any disclaimer, the term of this patent is extended or adjusted under 35 U.S.C. 154(b) by 1135 days.

(21) Appl. No.: 11/462,924

(22) Filed: Aug. 7, 2006

(65) Prior Publication Data
US 2006/0270028 A1 Nov. 30, 2006

Related U.S. Application Data

(63) Continuation of application No. 10/699,183, filed on Nov. 1, 2003, now abandoned.

(51) Int. Cl.
- A01N 1/00 (2006.01)
- A01N 1/02 (2006.01)
- C12M 1/00 (2006.01)
- C12M 3/00 (2006.01)

(52) U.S. Cl. .............. 435/284.1; 435/289.1; 435/297.2; 435/299.1; 435/304.2; 435/305.1; 435/305.4; 435/394; 435/1.1; 435/1.2; 600/36; 623/915; 623/916; 623/917; 623/918; 623/919; 623/920; 623/921; 623/922; 623/923

(58) Field of Classification Search .............. 435/305.4, 435/1.1, 284.1, 289.1, 297.2, 299.1, 304.2, 435/305.1, 394, 1.2; 623/915, 916–923; 600/36
See application file for complete search history.

(56) References Cited

U.S. PATENT DOCUMENTS

| | | | |
|---|---|---|---|
| 5,153,136 A * | 10/1992 | Vandenburgh | ........... 435/286.1 |
| 5,702,941 A | 12/1997 | Schwarz | |
| 5,792,603 A | 8/1998 | Dunkelman et al. | |
| 5,846,828 A | 12/1998 | Peterson et al. | |
| 5,888,807 A | 3/1999 | Palsson et al. | |
| 5,928,945 A | 7/1999 | Seliktar et al. | |
| 5,952,828 A * | 9/1999 | Rossman et al. | ............ 324/318 |
| 6,008,049 A | 12/1999 | Naughton et al. | |
| 6,121,042 A | 9/2000 | Peterson et al. | |
| 6,218,182 B1 | 4/2001 | Naughton et al. | |
| 6,281,007 B1 | 8/2001 | Fofonoff et al. | |
| 6,287,340 B1 | 9/2001 | Atlman et al. | |
| 6,416,995 B1 | 7/2002 | Wolfinbarger | |
| 6,537,567 B1 | 3/2003 | Niklason et al. | |
| 2002/0106625 A1 | 8/2002 | Hung et al. | |
| 2003/0043690 A1 | 3/2003 | Holl | |
| 2004/0063206 A1 | 4/2004 | Rowley et al. | |
| 2004/0110278 A1* | 6/2004 | Okano et al. | ............. 435/287.2 |
| 2004/0235150 A1 | 11/2004 | Takagi et al. | |
| 2005/0009179 A1 | 1/2005 | Gemmiti et al. | |
| 2005/0032200 A1 | 2/2005 | Sun et al. | |

* cited by examiner

Primary Examiner—Nathan A Bowers
(74) Attorney, Agent, or Firm—Fitch, Even, Tabin & Flannery

(57) ABSTRACT

A bioreactor and a method for growing engineered tissue provide facing surfaces in a vessel for containing cell-culture media. The facing surfaces are equidistant and define a gap therebetween while providing substrates for cell tissue growth. By maintaining conditions within the vessel conducive to cell tissue growth and moving the surfaces relative to one another within such cell culture media, tissue growing thereupon is subjected to physiological flow and shear stress, preferably through the use of oscillating motion, and engineered tissue is produced.

15 Claims, 3 Drawing Sheets

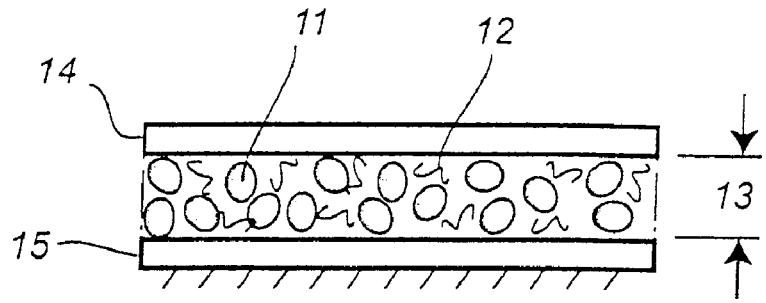
FIGURE 4A. Stasis
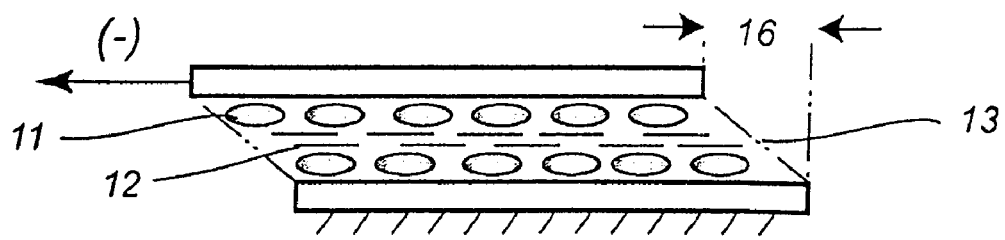
FIGURE 4B. (−) Displacement
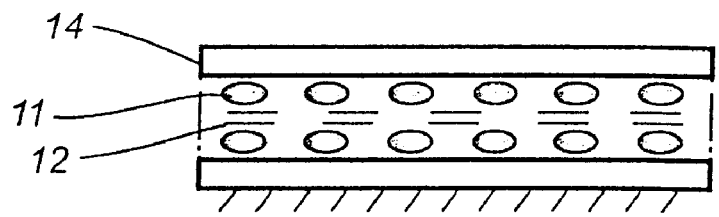
FIGURE 4C. Initial Position
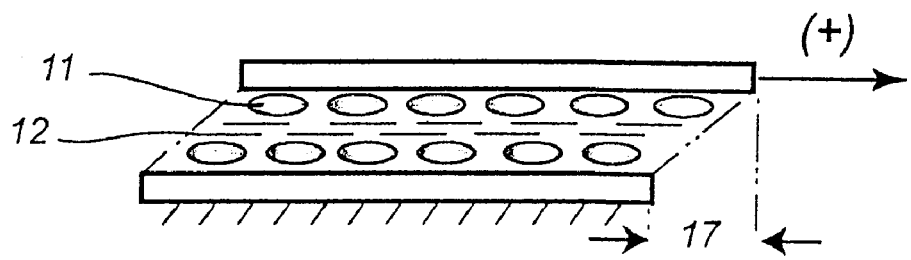
FIGURE 4D. (+) Displacement

BIOREACTOR FOR GROWING ENGINEERED TISSUE

This application is a continuation of U.S. Ser. No. 10/699,183, filed Nov. 1, 2003.

FIELD OF THE INVENTION

This invention relates to bioreactors for growing engineered tissue from cell cultures and more particularly to growing patch and vascular grafts from cultures of cells that will grow to produce such new structures.

BACKGROUND OF THE INVENTION

Synthetic tissues and vascular grafts are commercially available and have generally been made of polyethylene teraphthlate (PET), expanded polytetrafluroethylene and decellurized pericardium, and from harvested veins and arteries; they have also been constructed from naturally occurring molecules, such as collagens, elastins, chondritans and hyaluronins. However, more recently, efforts have been made to grow such graft materials, such as patches and vascular grafts, from cell cultures with varying degrees of success. U.S. Pat. No. 6,416,995 (Jul. 9, 2002), the disclosure of which is incorporated herein by reference, taught the creation of vascular grafts by recellularizing devitalized tissue materials by repopulating same in a bioreactor, using what is sometimes identified as a "constructionist" approach. It was pointed out that prior observations had suggested that the incubation of fibroblastic cells along with cardiovascular tissues should result in successful cellular penetration into the matrix structure, although some inducement might be required.

It had earlier been shown that red blood cells suspended in hyaluronic acid solutions will, when subjected to oscillating flow, readily orient and deform in the direction of flow (see More R B, Red Blood Cell Deformation in Oscillatory Flow, Thesis, University of Texas at Austin, 1997). Similar flow orientational phenomena occur in suspensions of ellipsoidal particles, rod-like particles (see Jeffery G B, The Motion of Ellipsoidal Particles Immersed in a Viscous Fluid, Proc Roy Soc, 1923; A102:161-175) and fluid droplets in emulsions (see Taylor G I, The Formation of Emulsions in Definable Fields of Flow, Proc Roy Soc, 1934; A146:501-523). Moreover, it is felt that this shear stress-deformation phenomena is ubiquitous to all cells, and thus is applicable to endothelial cells, fibroblasts and osteocytes.

U.S. Pat. No. 5,792,603 describes a bioreactor and a method for seeding and culturing a vascular graft where alternating pressure is applied to a support structure, e.g. a radial sheer stress is applied to a scaffold designed to create a vascular graft. Such techniques are believed to more effectively grow cells and tissue if such are adapted to the physical environment in which they find themselves, and thus it is believed that creating physiological flows and stresses can provide important components in defining ultimate tissue configuration. Accordingly, it is believed worthwhile to apply flows and stresses of the type that will be expected to be encountered in the proposed end use environment so that engineered tissue can be grown and cultured in a manner that will provide such with the best ultimate structure. This concept is also recognized in U.S. Pat. No. 5,928,945 (Jul. 27, 1999) where tissue-engineered cartilage was produced, the disclosure of which is also incorporated by reference; a sheer flow stress was used to grow artificial cartilage on an artificial substrate in a bioreactor.

As illustrated in these patents, such tissue engineering processes have involved the use of the pumps and circulating flow systems, e.g., where a reservoir of growth media feeds a circulating pump which maintains a constant flow through a growth chamber, as described in the '945 patent. In the '995 patent, peristaltic pumps supply solutions to a bioreactor, and pulsative flows are achieved using a pulsatile pump. While such systems have demonstrated the validity of the premise of achieving improved growth of tissue grafts through the use of shear flows and stresses, simpler systems have continued to be sought.

SUMMARY OF THE INVENTION

An improved device and method are provided for applying stresses to cells being cultured, as well as to the constituents of a scaffolding substrate upon which cells are being simultaneously cultured, or may be subsequently cultured, so as to simulate the physiological environment of an extracellular matrix in which the cells are to be embedded. Overall, the invention provides a mechanism to organize and preferentially orient cells and scaffolding constituents, which is one that may also be used to promote the formation of multiple cellular layers. The invention provides an apparatus for cell culture that uses the principle of oscillating flow between surfaces equidistant from each other, e.g. parallel plates, coaxial tubes, etc., as a mechanism for localizing, orienting, and applying stress to define the net shape of an array of cells in culture and/or the molecular constituents of scaffolding for the production of engineered tissues. Very generally, a suspension of cells and/or scaffolding constituent molecules is placed within a gap between two equidistant surfaces and either (1) one surface is oscillated and one is held fixed, or (2) both surfaces are simultaneously oscillated in opposite directions. Fluid interfaces at the edges of the surfaces provide diffusion paths for the exchange of nutrients and waste.

In one particular aspect, the invention provides a bioreactor for growing engineered tissue, which bioreactor comprises a vessel for containing cell-culture media, a pair of approximately parallel, approximately equidistant, surfaces which define a gap and provide substrates for cell tissue growth to occur within such gap, means for maintaining conditions within said vessel conducive to cell tissue growth, and means for moving said surfaces relative to one another within media supplied to said vessel so as to subject tissue growing upon and between the surfaces to physiological flow and to shear stress.

In another particular aspect, the invention provides a method for growing engineered tissue, which method comprises providing facing surfaces in a bioreactor vessel, supplying said vessel with cell-culture media under conditions conducive to cell tissue growth, and maintaining relative movement between said facing surfaces so as to subject cell tissue growing upon said surfaces to physiological flow and shear stress.

BRIEF DESCRIPTION OF THE DRAWINGS

FIG. 2A is a top view of the coaxial cylinder and tube shown in FIG. 2.

FIGS. 4A-4D are schematic views showing the effects of relative movement between a pair of plates on cell media located between such pair of plates.

DETAILED DESCRIPTION OF THE PREFERRED EMBODIMENTS

Figure 1:
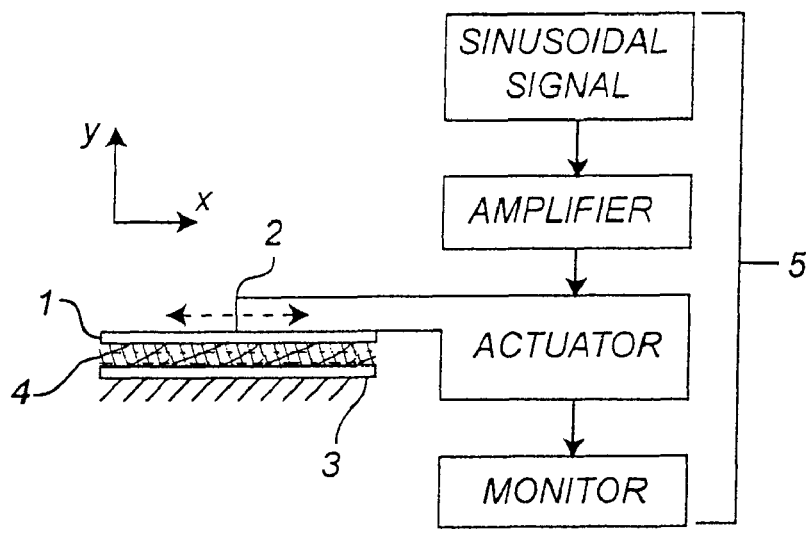
FIG. 1 is a schematic view of a system that might be employed for operating a bioreactor to grow engineered tissue embodying various features of the invention, employing a pair of oscillating parallel plates and a suitable electro-mechanical drive mechanism.

It is known that linear molecules and cells in suspensions align with and are deformed by flow which occurs in the vicinity thereof. Thus, suspensions of cells and/or scaffolding components, such as collagen molecules, can be preferentially and uniformly oriented by taking advantage of this characteristic. The width of a gap D between equidistant surfaces and the surface geometry will control the ultimate thickness and shape of the resulting cellular or scaffolding array that is produced. The culture media which may be employed includes simple aqueous saline solutions or nutrient broth; however, cells and molecules can also be suspended in viscoelastic, high molecular weight, polymeric hydrogels and in mixed molecular solvents, e.g., those including hyaluronic acid, chondritan, dextran, xanthane, polylactic acid, collagen, polyvinyl pyrolidone, and the like. Such high viscoelastic solvents may be advantageous because they tend to trap or embed suspended cells or molecules; thus, they can act as a medium for transmission of flow and shearing stresses while also providing a diffusion path for nutrients and in this manner can simulate some of the functions of an extracellular matrix.

The degree of flow-induced cellular or scaffolding substrate deformation and orientation depends upon the magnitude of the applied stress, which magnitude in turn depends upon the viscoelasticity of the suspending solvent along with the magnitude and the frequency of the oscillation of the surfaces. Because cells and linear molecules are viscoelastic entities, such deformation that is applied may reach a quasi-steady state if the period of cyclic oscillation is on the order of a nominal suspension relaxation time. For isolated cells in simple viscous Newtonian aqueous media, the relaxation time is approximately 0.1 second. If flow stresses are removed for a time period exceeding the relaxation time, the cell suspension orientational state rapidly returns to the original unstressed state. Therefore, in steady flow, it is necessary to continuously apply the shearing stresses, which requires constant pumping and a relatively large nutrient media volume.

However, the relaxation time may be extended to approximately 1 second by suspending the cells and linear molecules in a viscoelastic solvent, such as a 0.5 wt % hyaluronic acid or a 1% hyaluronic acid solvent, which can extend the relaxation time out to approximately 10 seconds (see More thesis). Other viscoelastic additives such as chondritan, dextran, xanthane, polylactic acid, collagen, polyvinyl pyrolidone, and the like produce a similar effect. Thus, by rendering the solvent viscoelastic, the suspension relaxation time is increased and the stressed orientational state is maintained in time, allowing the use of a gentle, sinusoidal, cyclic oscillating flow as the means of stress application. Use of a viscoelastic media mimics the natural situation in which cells in a tissue are surrounded by other viscoelastic cells and by the viscoelastic extracellular matrix instead of a simple viscous Newtonian growth media.

In addition to assuming such preferential orientation, it is found that such flow produces an organized state in which alternating layers of cells and cell-free solvent regions occur across the plate gap at strain levels in excess of one, where strain is the ratio of the magnitude of oscillation to the width of the gap between equidistant surfaces. This has been demonstrated for blood suspension (see Thurston G B, Plasma release-cell layering theory for blood flow, Biorheology, 1989; 26:199-214) and should likewise occur both for the suspension of other types of cells and for the suspension of scaffolding constituent molecules. In this respect, the invention provides a mechanism to promote the formation of multi-layer tissue structures as well as simple monolayer structures.

It is thus been found to be feasible to apply flow and shearing stresses of meaningful physiological magnitudes, for suitable time scales, to arrays of cells and/or scaffolding constituents in cell cultures by using such mechanical plate oscillations and thus avoid the need for elaborate pumping and circulating flow systems. The gaps between the equidistant surfaces define the net orientation and thickness of the cultured tissue or scaffolding, and the surface size and shape of course determines the size and shape of resultant tissue. Because sinusoidal oscillating flow results in net zero displacement and because of the hydrodynamic principal of 'no slip', the entire suspension should remain between the equidistant surfaces at all times, thus spatially confining the cells being cultured. As a result, a large recirculating volume of nutrient broth is not required, as was needed in certain prior art systems; however, by keeping the interfaces at plate edges, for example, open to the surrounding fluid culture, and or by employing a gas-permeable membrane as one of the plates, the exchange of nutrients and waste material at such locations is facilitated. Furthermore, more complex drive waveforms such as a saw tooth, ramp, square and more general pulsatile forms can be synthesized by Fourier superposition of simple sinusoids.

Cells may be cultured in place between parallel plates for example and permitted to produce their own attachments and scaffolding. In such a situation, the net shape, thickness and the layering of the resultant tissue will be determined by the gap between the plates and the plate drive configuration. Shown in FIG. 1 is a schematic representation including a pair of such parallel plates as might be used within a bioreactor to grow engineered tissue. The upper plate (1) is depicted as oscillating (2) in the x-direction in a sinusoidal fashion relative to the lower fixed plate (3) at a selected cyclic radian frequency, $\omega=2\pi f$, where f is the frequency in Hertz. The cells and/or scaffolding suspension (4) is contained within the gap, D, between the plates. The upper plate oscillation is produced by the electro-mechanical actuator system (5) as known in the general art. This geometric and mechanical configuration produces a spatially uniform shearing stress across the plate gap described as follows. The velocity, v, and displacement x, of the moving plate are calculated as in the Thurston article, supra:

$$v = v_m \cos(\omega t) \tag{1}$$

-continued $$x = \frac{v_m}{\omega}\sin\left(\omega t - \frac{\pi}{2}\right)$$

where the subscript m denotes a sinusoidal magnitude. For a uniform velocity gradient across the plate gap the shear rate, $\gamma'$, and shear strain, $\gamma$, are defined as:

$$\gamma' = \frac{v_m}{D}\cos(\omega t) \quad (2)$$

$$\gamma = \frac{v_m}{\omega D}\cos\left(\omega t - \frac{\pi}{2}\right)$$

This geometric and mechanical configuration produces a spatially uniform viscoelastic shear stress wave across the plate gap of wavelength, $\lambda$, $$\lambda = \frac{2\pi\left[\frac{\eta_m}{\rho\omega}\right]^{\frac{1}{2}}}{\cos\left(\frac{\phi}{2} - \frac{\pi}{4}\right)} \quad (3)$$

where $\rho$ is the suspension density, $\eta_m$ is the magnitude, and $\phi$ is the phase of the complex modulus of viscosity. For the condition that D is small with respect to the shear wavelength, the velocity gradient in the gap is essentially constant (see Schrag et al. article, supra). Therefore, the shear stress is uniform across the gap for a given drive state in the parallel plate system. For example, parallel plate geometry can be employed to produce uniformly stressed arrays of planar tissue sheets, such as useful for vascular patches, the creation of leaflets for valve prostheses, collagen sheets, cartilage sheets, skin grafts, and burn and wound-healing dressings.

Figure 2:
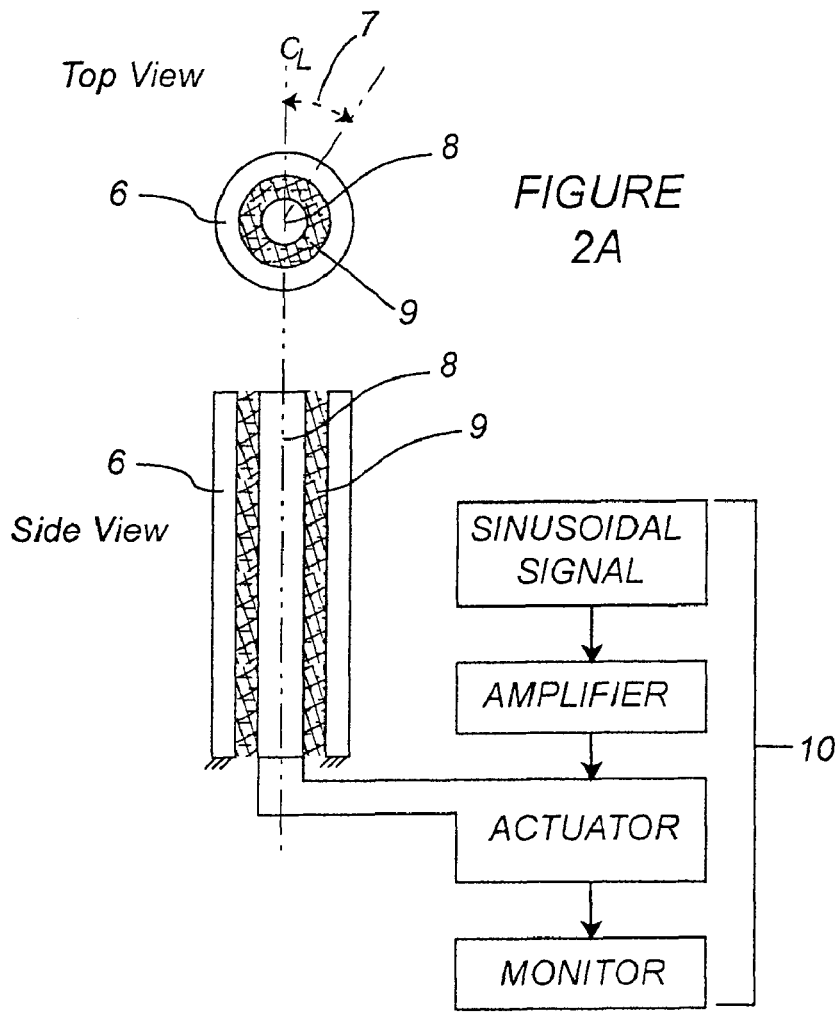
FIG. 2 is a schematic side view showing a coaxial cylinder within a tube that are being moved in oscillating motion, in respect to each other, by an appropriate drive system, which arrangement could be employed in the bioreactor of FIG. 1 in place of the parallel plate structure therein illustrated.

Shown in FIGS. 2 and 2A is an alternative embodiment where, instead of a pair of parallel plates, a pair of coaxial cylindrical surfaces are employed, such as those presented by a coaxial cylinder and surrounding tube arrangement. An outer cylinder (6) is fixed while an inner cylinder (8) is caused to rotate in oscillation. A cell and/or scaffolding suspension (9) is contained in the annular gap between the to cylindrical surfaces. The inner cylinder oscillation is produced by an electro-mechanical actuator system (10) as known in this art. Like the parallel plate configuration of FIG. 1, this geometric configuration also produces a spatially uniform shearing stress across the annular gap. Such coaxial cylinder/tube geometry is useful to produce uniformly stressed tubular arrays that might be employed as tendons, vein or artery grafts or replacements.

In addition, the use of pairs of surfaces with arbitrary geometries may be employed; for example, such may be used to produce sinuses for an aortic valve or even an entire, shaped heart valve or a bicuspid venous valve.

It is also possible to produce spatially oriented arrays of scaffolding molecules using constituents such as collagen or mixtures containing hyaluronic acid, cholesterol, heparin or the like, using such a oscillating plate or cylindrical surface apparatus. Once such an oriented scaffolding is created, it may be fixed in its structure by exposure to chemicals or photo oxidation that is designed to create cross-linking, or such may be less unfixed if desired. Either simultaneous with the creation of such a scaffolding or subsequent thereto, cells can be provided within such an oscillating environment; in either event, will attach to and/or embed themselves in such scaffolding between the oscillating surfaces.

Depending upon the intended subsequent use of the tissue being engineered, it may be desirable to include certain ancillary agents in the fluid culture. It has been found that, by embedding in such tissue or scaffolding matrix, agents such as liposomes that contain encapsulated enzymes, insulin or certain organ-specific secretory cells, tissue which is particularly targeted for organ replacement or for organ enhancement may be grown.

The bioreactor may be a chamber of any desired to size and shape, dependent upon the character of the resultant tissue that one is seeking to engineer. Such bioreactors are well known and are disclosed in the previously mentioned U.S. patents. Generally, the bioreactor would be maintained at a temperature between about 35° C. and 38° C. so as to that would be particularly conducive to cell growth. Although orientation of the equidistant surfaces may not be of primary concern, they are preferably vertically oriented to take advantage of gravity in the diffusion of nutrients and waste. Such an orientation is preferred both for parallel plates and for other arrangements, such as a cylinder of circular cross section within a surrounding tube. The facing surfaces may oscillated in any suitable direction; however for parallel plates, the oscillation is preferably in the horizontal plane. For equidistant cylindrical surfaces, such as two surfaces that are oriented with their axes vertical, there is preferably relative rotation about the common axis to again create the forces in horizontal planes; however, for growing certain specific structures, it may be useful to carry out the oscillation along a common axis.

The plates or cylinder and tube can be driven in such oscillating movement by a suitable electromagnetic drive system, such as that described in a 1965 article entitled, "Shear-wave interference observed by optical birefringence induced in a viscoelastic Liquid" by Schrag et al. *J. Applied Physics,* 1965; 36(4):1996-2000. Such is depicted as item 5 in FIG. 1. The control of the drive may be carried out using a suitable mechanical, digital or analog electronic waveform generator. Although for simplicity of control it may be desirable to move only one of the facing surfaces, as shown in FIGS. 1 and 2, both surfaces could be simultaneously moved in opposite directions.

One example of growing cells that might be of use as a human patch graft is set forth hereinafter; however, it should be understood that this example merely describes a presently preferred method for using the invention and does not constitute limitations upon its scope which is defined by the claims at the end of this description.

Example 1

A thin planar connective tissue array of approximately 0.5 mm thickness, 50 mm width by 50 mm length, as desired for a graft patch or for use in heart valve leaflet repair, may be prepared by incubating fibroblasts in a standard nutrient medium, such as Dulbecco's modified Eagles medium, within a bioreactor. Nutrient media for the culture of mammalian cells are well known in the art and contain essential nutrient and supplements as may be appropriate for the particular cell type grown. The tissue array dimensions are arbitrarily determined by the size of the oscillating plates: 50 mm square and plate gap thickness D of 0.5 mm used in this example.

From a rheological perspective, standard aqueous nutrient media behaves as a purely viscous Newtonian fluid with a viscosity on the order of 1 to 2 centipoise (cP). Addition of a proteoglycan such as hyaluronic acid to an approximate concentration of 0.5 mg/ml (0.5%) renders the growth media highly non-Newtonian and viscoelastic.

Figure 3A:
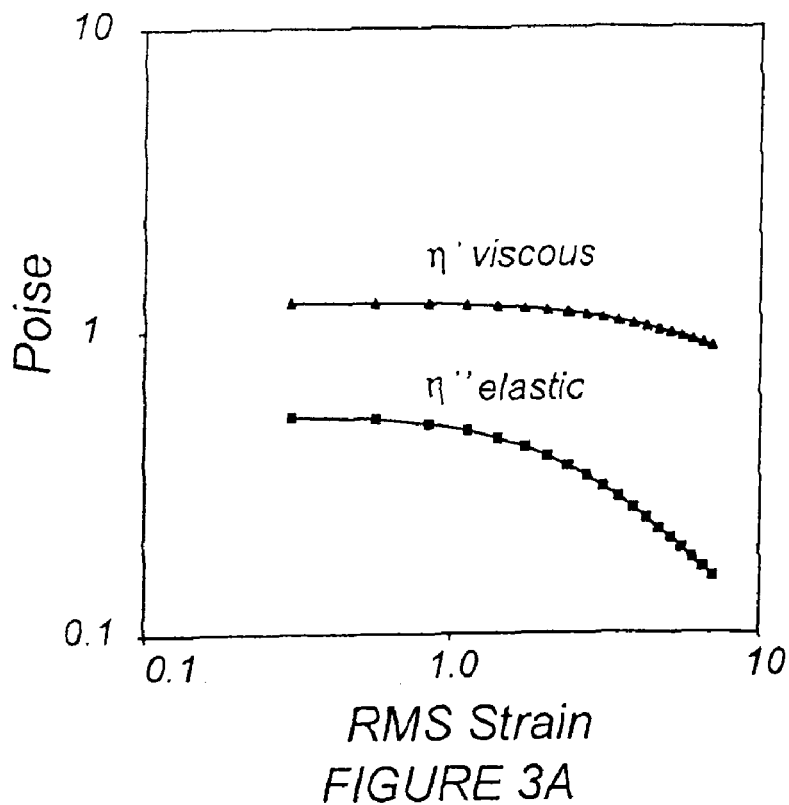
FIG. 3A is a plot of the viscous and elastic components of the complex modulus of viscosity of a 0.5% aqueous hyaluronic acid solution as a function of root mean square strain oscillatory strain magnitude measured at a cycle frequency of 2 Hz.
Figure 3B:
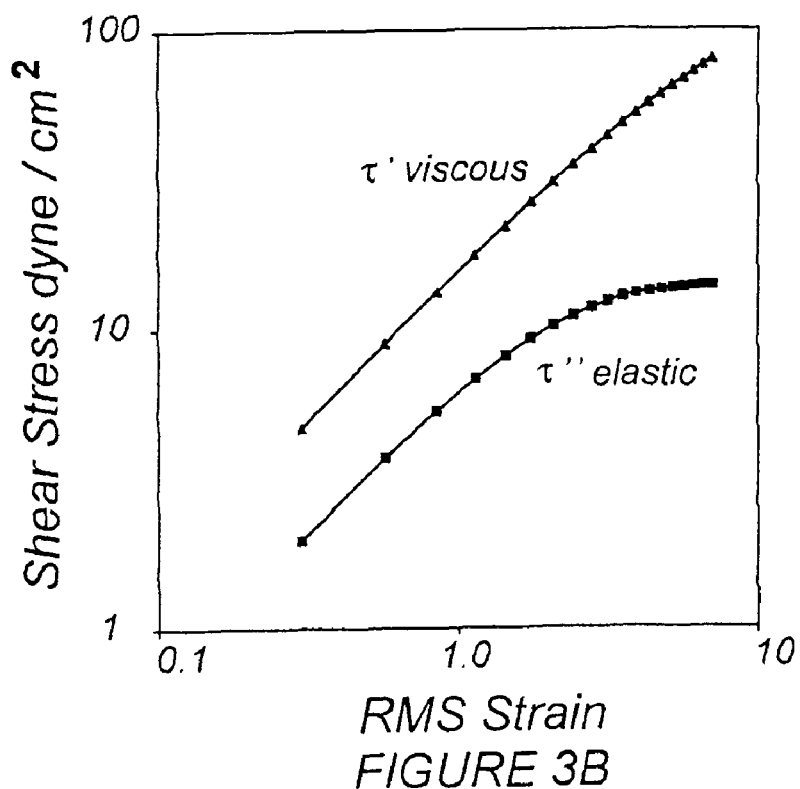
FIG. 3B is a plot of the viscous and elastic shear stresses developed in the same aqueous hyaluronic acid solution as a function of root mean square strain oscillatory strain magnitude measured at a cycle frequency of 2 Hz.

Shear stress levels developed within suspensions cultured in the parallel plate apparatus are determined by inference using independent measurements of the nutrient media complex modulus of viscosity, or equivalently the complex modulus of rigidity. For example, FIG. 3A shows the viscous and elastic components of the complex modulus of viscosity, $\eta^*$, measured using a Vilastic-3 viscoelasticity analyzer, for a 0.5% Hyaluronic acid solution tested at an oscillatory frequency of 2 Hz as a function of strain rate (More, 1997). Data in FIG. 3A and FIG. 3B are presented as functions of root mean square (RMS) sinusoidal strain $\gamma$ magnitude because strain is conceptually convenient for the parallel plate apparatus. From EQN 1 and EQN 2, the sinusoidal strain magnitude $\gamma_m$ is the ratio of the sinusoidal displacement magnitude $x_m$ to the gap width D as $\gamma_m = x_m/D$. With EQN 2, $\gamma$ is directly proportional to strain rate $\gamma'$ as: $\gamma' = \omega \gamma$.

From the 0.5% hyaluronic solution Vilastic 3 measurements, the coefficients of the complex modulus of viscosity $\eta^* = \eta' - i\eta''$ were calculated, where $\eta'$ is the real, viscous component and $\eta''$ is the imaginary, elastic component (Thurston, 1976). Measurements of $\eta^*$ include shear stresses according to the definition of the complex modulus as ratio of the shear stress, $\tau^*$, to shear rate, $\gamma'^*$, $$\eta^* = \frac{\tau^*}{\gamma'^*} \qquad (4)$$
$$= \eta' - i\eta''$$
$$= \eta_m e^{i(\omega t - \phi)}$$

With the phase angle of the shear rate arbitrarily set to 0, $\phi$ is the phase angle between the shear rate and shear stress at the radian frequency $\omega$; $\gamma'_m$ and $\tau_m$ are magnitudes of the complex shear rate and shear stress.

$$\gamma'^* = \gamma'_m e^{i\omega t}$$
$$\tau^* = \tau_m e^{i(\omega t + \phi)} \qquad (5)$$

The corresponding shear stresses developed in the hyaluronic acid enriched nutrient solution, for a plate gap of 0.05 cm with the plate oscillated at a nominal physiological frequency of 2 Hz, are shown in FIG. 3B. Addition of type 1 collagen, with an estimated intrinsic viscosity of 16 dl g$^{-1}$ (see Fujimoto D., Biochem Biophys Acta 1968; 168:537), to a concentration of 0.3 mg/ml should result in a nutrient media suspension with a real viscous component of approximately 1.73 P at a RMS strain of approximately 1 for the 2 Hz oscillation. The corresponding real component of the oscillatory shear stress will be on the order of 30 dyne/cm$^2$, which is within the physiological range of interest for the arterial cardiovascular system. Innoculating the nutrient suspension with 1 million to 4 fibroblasts per ml and incubating at 37 C and a physiological pH of 7.4 should produce a confluent layer of cells within approximately 24 to 48 hours and a multilayer planar tissue array within approximately 96 hours in which the fibroblasts and collagen fibrils are preferentially oriented in the shear direction.

Use of the concentric cylinder system depicted in FIG. 2, instead of the parallel plate system, and including endothelial cells would produce a tubular array suitable for the repair or replacement of a vein, artery or some other tubular structure. Substituting chondrocytes for fibroblasts and chondritan for hyaluronic acid in the above example will produce a tissue array appropriate for the replacement of cartilage or tendon.

FIGS. 4A-4D provide a schematic showing the behavior of the suspended cellular solution parallel plate apparatus as the upper plate oscillates in a sinusoidal fashion. FIG. 4A shows the arrangement in stasis where the cells (11) and scaffolding molecules (12) within the plate gap (13) are randomly distributed and not subjected to flow stresses so long as the plates (14, 15) are stationary. When the upper plate is displaced (16) relative to the lower plate, as shown in FIG. 4B, the cells (11) and molecules (12) deform and assume a preferential orientation relative to the flow-related shearing stresses. The suspension remains within the gap (13) and moves with the plates throughout plate motion according to the hydrodynamic principal of 'no slip'. As the plate (14) returns to and moves through the initial position, see FIG. 4C, the viscoelastic cells (11) and molecules (12) retain a quasi-steady state deformation and orientation according to the suspension relaxation time. As the plate is then displaced in the reverse direction (17) in FIG. 4D, the cells (11) and molecules (12) are symmetrically deformed and aligned as before during plate displacement in the opposite direction. Because the shear distribution is uniform across the gap, the orientation and alignment of the cellular and molecular constituents is uniform throughout the gap. Flow-induced structure, such as the preferential orientation and layering of cells relative to the solvent, may occur when the unit strain level is exceeded. The induced shear stress levels are a function of the plate displacement, velocity, magnitude, oscillation frequency and the suspension viscoelasticity. This shear stress level is preferably matched to the expected service stresses for the engineered tissue. As the cells reproduce, cellular attachments are formed, additional extracellular constituents are produced and secreted to form a stable preferentially oriented and stressed extracellular matrix and cellular array. The dimensions of the resulting engineered tissue array are determined by the size of the plates and the gap between the plates. Different specific tissue types can be prepared by varying the cell type, solvent constituents, plate geometry and induced shear stress levels.

While the examples given assume a simple sinusoidal plate motion, more complex waveforms such as a sawtooth, ramp, square or more a general pulsatile form can be synthesized by Fourier superposition of sinusoids. Furthermore, a gas exchange capability for oxygenation can be realized by using a gas permeable membrane for the stationary plate.

While the invention has been described with regard with certain preferred embodiments, which constitute the best mode presently known to the inventor for carrying out this invention, it should be understood the various changes and modifications as would be obvious as one having the ordinary skill in its art may be made without departing from the scope of the invention which is defined by the claims appended hereto. The disclosures of the U.S. patents and articles referenced herein are expressly incorporated herein by reference.

The invention claimed is:
1. A bioreactor for growing engineered tissue, which bioreactor comprises:
a vessel for containing cell-culture media,
a pair of flat parallel plates which are substantially equidistant from each other and define a constant uniform gap therebetween, said plates serving as substrates upon which cell tissue growth may occur within such gap,
culture media within said vessel conducive to cell tissue growth, and an electromechanical drive mechanism which moves both said plates relative to one another to create oscillating motion within said culture media supplied to said vessel while maintaining said constant uniform gap so as to subject cell tissue growing upon and between said plates to physiological flow and to shear stress caused by the generation of a spatially uniform viscoelastic standing shear stress wave across said constant uniform gap.

2. The bioreactor of claim 1 wherein one of said flat plates is gas-permeable.

3. A method for growing engineered tissue, which method comprises:
provicing two facing flat plates in a bioreactor vessel spaced apart by a constant uniform gap,
supplying said vessel with cell-culture media under conditions conducive to cell tissue growth, and
maintaining relative oscillating movement between said facing flat plates by moving both said plates with the uniform gap therebetween maintained constant so as to subject cell tissue growing upon facing surfaces of said plates to physiological flow and to shear stress caused by the generation of a spatially uniform viscoelastic standing shear stress wave across said constant uniform gap.

4. The method of claim 3 wherein both said facing surfaces of said flat plates are caused to move in opposite directions to create said oscillating motion.

5. The method of claim 3 wherein the period of oscillation of said surfaces is about 20 seconds or less.

6. The method of claim 3 wherein the oscillating motion is carried in a generally horizontal direction.

7. The method of claim 3 wherein said vessel is supplied both with cell culture media and with scaffolding constituents as a result of which scaffolding and tissue are simultaneously grown between or on said facing surfaces of said flat plates.

8. The method of claim 3 wherein said cell culture media is supplied in a viscous or viscoelastic solvent having a viscosity of at least about 1 centiPoise.

9. The method of claim 3 wherein one of said flat plates is gas-permeable.

10. The method of claim 3 wherein a shear stress in the range of about 10 to 1000 dynes/cm$^2$ is applied.

11. The method of claim 10 wherein said tissue growing on said facing surfaces of said flat plates is subjected to a strain level in excess of 1, with such strain being the ratio of the magnitude of oscillation to the width of the gap between the facing flat plates.

12. The method of claim 3 wherein said spacing between said equidistant facing flat plates is between about 1 micrometer and about 5 millimeters.

13. The method of claim 3 wherein conditions are employed so as to grow a multilayered tissue material.

14. The method of claim 6 wherein said flat plates are oriented in a vertical direction.

15. The method of claim 3 wherein said oscillating movement between said flat plates produces a spatially uniform viscoelastic shear stress wave across said constant uniform plate gap of wavelength λ, wherein $$\lambda = \frac{2\pi \left[\frac{\eta_m}{\rho\omega}\right]^{\frac{1}{2}}}{\cos\left(\frac{\phi}{2} - \frac{\pi}{4}\right)}$$

where ρ is the suspension density, $\eta_m$ is the magnitude, and φ is the phase of the complex modulus of viscosity.

* * * * *